(12) United States Patent
Marinier et al.

(10) Patent No.: US 7,470,713 B2
(45) Date of Patent: Dec. 30, 2008

(54) IMIDAZOLE BASED KINASE INHIBITORS

(75) Inventors: Anne Marinier, Kirkland (CA); Stephan Roy, St. Lambert (CA); Alain Martel, Delson (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 560 days.

(21) Appl. No.: 11/062,271

(22) Filed: Feb. 18, 2005

(65) Prior Publication Data

US 2005/0187218 A1    Aug. 25, 2005

Related U.S. Application Data

(60) Provisional application No. 60/546,814, filed on Feb. 23, 2004.

(51) Int. Cl.
*A61K 31/4439*    (2006.01)
*C07D 401/04*    (2006.01)

(52) U.S. Cl. .................................. 514/341; 546/274.1

(58) Field of Classification Search .............. 546/274.1; 514/341
See application file for complete search history.

(56) References Cited

U.S. PATENT DOCUMENTS 6,207,687 B1    3/2001    Claiborne et al.

OTHER PUBLICATIONS

Vippagunta et al., "Crystalline Solids", Advanced Drug Delivery Reviews 48 (2001) 3-26.*
Guillory, "Generation of, etc.," in Britain ed, Polymorphism in Pharmaceutical Solids, NY: Marcel Dekker, Inc., 1999 183-226.*
Balant, Metabolic Considerations, etc., in Wolff ed, Burger's Medicinal Chemistry and Drug Discovery, 1995, NY: John Wiley & Sons, Inc.*

* cited by examiner

*Primary Examiner*—Patricia L Morris
(74) *Attorney, Agent, or Firm*—Hong Liu; Maureen S. Gibbons

(57) ABSTRACT

The present invention provides compounds having formula I

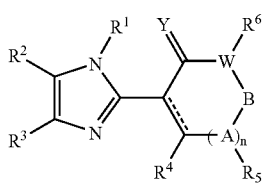

and their use for the treatment of cancer.

12 Claims, No Drawings

IMIDAZOLE BASED KINASE INHIBITORS

RELATED APPLICATIONS

This application claims priority benefit under Title 35 § 119(e) of U.S. provisional Application No. 60/546,814, filed Feb. 23, 2004, the contents of which are herein incorporated by reference.

BACKGROUND OF THE INVENTION

The present invention relates to compounds which inhibit tyrosine kinase enzymes, compositions which contain tyrosine kinase inhibiting compounds and methods of using inhibitors of tyrosine kinase enzymes to treat diseases which are characterized by an overexpression or upregulation of tyrosine kinase activity such as cancer, diabetes, restenosis, arteriosclerosis, psoriasis, angiogenic diseases and immunologic disorders (Powis, G.; Workman, P. Signaling targets For The Development of Cancer Drugs. *Anti-Cancer Drug Design* (1994), 9: 263-277; Merenmies, J.; Parada, L. F.; Henkemeyer, M. Receptor Tyrosine Kinase Signaling in Vascular Development. *Cell Growth Differ* (1997) 8: 3-10; Shawver, L. K.; Lipsosn, K. E.; Fong, T. A. T.; McMahon, G.; Plowman, G. D.; Strawn, L. M. Receptor Tyrosine Kinases As Targets For Inhibition of Angiogenesis. *Drug Discovery Today* (1997) 2: 50-63; all herein incorporated by reference).

In addition to being used as single agents, it is contemplated that tyrosine kinase inhibitors can enhance the activity of cytotoxic or cytostatic treatments when used in combination with standard therapies known in the art.

SUMMARY

The present invention is directed to compounds having the formula I:

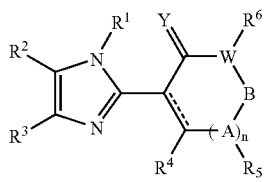

I their enantiomers, diastereomers, pharmaceutically acceptable salts, hydrates, or esters thereof wherein:

n is 0, 1, 2, or 3;

Y is O or S;

A and B are independently —CH, N, or CO, provided that A and B are not both CO;

W is N, CH, O or S provided that when W is O or S, $R^6$ is absent;

$R^1$, $R^3$, and $R^6$ are each H or $C_1$ to $C_6$ alkyl;

$R^2$ is H, $C_{1-6}$ alkyl, $C_{2-6}$ alkenyl, $C_{2-6}$ alkynyl, $C_{3-6}$ cycloalkyl, heterocycloalkyl, halo, amino, aminoalkyl, alkoxy, thioalkoxy, nitro, aryl, heteroaryl, alkoxyalkyl, thioalkoxyalkyl, aralkyl, heteroarylalkyl, heterocycloalkylalkyl, —CN, —C(O)$R^8$, —CO$_2R^8$, —CONR$^9R^{10}$, —CO$_2$NR$^{11}R^{12}$, —NR$^{13}$CONR$^{14}R^{15}$, —NR$^{16}$SO$_2R^{17}$, —SO$_2$NR$^{18}R^{19}$, —C(NR$^{20}$)NR$^{21}R^{22}$;

$R^4$ and $R^5$ are each H, —NH-Z, —NH-Z-aryl, or NH-Z-heteroaryl, wherein

Z is selected from the group consisting of $C_1$-$C_4$ alkyl, alkenyl, and alkynyl; Z optionally having one or more hydroxy, thiol, alkoxy, thioalkoxy, amino, halo, NR$^{23}$SO$_2R^{24}$, —CO, —CNOH, —CNOR$^{26}$, —CNNR$^{27}$, —CNNCOR$^{28}$ and —CNNSO$_2R^{29}$; and $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and $R^{26}$ are independently selected from the group consisting of H, alkyl, alkenyl, alkynyl, cycloalkyl, cycloalkylalkyl, hydroxy, alkoxy, aryl, heteroaryl, heterocyclyl, heteroarylalkyl, and alkyl-$R^{25}$ wherein $R^{25}$ is alkenyl, hydroxy, thiol, alkoxy, thioalkoxy, amino, alkylamino, dialkylamino, aryl, heteroaryl, cyano, halo, heteroaryl, heterocyloalkyl, sulfoxy, sulfonyl, —NR$^{27}$COOR$^{28}$, —NR$^{29}$C(O)R$^{30}$, —NR$^{31}$SO$_2R^{32}$, SO$_2$NR$^{32}$ R$^{32}$—C(O)NR$^{33}R^{34}$, and $R^{27}$, $R^{28}$, $R^{29}$, $R^{30}$, $R^{31}$, $R^{32}$, $R^{33}$, and $R^{34}$ are, independently, hydrogen, alkyl, or cycloalkyl.

According to one embodiment of the present invention, A and B are carbon.

According to some embodiments of the present invention, $R^3$ is H, methyl, or ethyl.

According to one embodiment of the present invention, $R^4$ is —NH-Z-aryl or $R^4$ is —NH-Z-heteroaryl.

In one embodiment of the present invention, Y is O; $R^1$, $R^3$, $R^5$, $R^6$ are each independently H or $C_{1-6}$ alkyl; $R^2$ is aryl, heterocycloalkylaryl, heteroaryl, cycloalkyl or heterocycloalkyl; and $R^4$ is —NH-Z-aryl or —NH-Z-heteroaryl.

In some embodiments of the present invention, $R^2$ is an aryl, such as phenyl or substituted phenyl, an optionally substituted heterocycloalkyl, such as piperidine, piperazine, or morpholine, —C(O)$_2$-alkyl, or —CONR$^9R^{10}$ wherein $R^9$ and $R^{10}$ are independently H, $C_{1-6}$ alkyl, cycloalkyl, cycloalkylalkyl, aryl, heteroaryl, heterocycloalkyl, heteroarylalkyl or alkyl-$R^{25}$.

The present invention is further directed to methods for treating a condition associated with at least one tyrosine kinase enzyme comprising administering to a mammal in need thereof a therapeutically effective amount of a compound of formula I.

According to one embodiment of the present invention, methods of treating cancer are provided comprising administering to a mammal in need thereof a therapeutically effective amount of a compound of a Formula I, and optionally administering at least one additional anticancer agent.

The present invention also provides pharmaceutical compositions comprising a compound of Formula I together with a pharmaceutically acceptable carrier.

DETAILED DESCRIPTION OF THE INVENTION

As used herein, the term "alkyl" herein alone or as part of another group refers to a monovalent alkane (hydrocarbon) derived radical containing from 1 to 12 carbon atoms unless otherwise defined. An alkyl group is an optionally substituted straight, branched or cyclic saturated hydrocarbon group. When substituted, alkyl groups may be substituted with up to four substituent groups, at any available point of attachment. When the alkyl group is said to be substituted with an alkyl group, this is used interchangeably with "branched alkyl group". Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: hydroxy, halo (such as F, Cl, Br, I), haloalkyl (such as CCl$_3$ or CF$_3$), alkoxy, alkylthio, cyano, carboxy (—COOH), alkylcarbonyl (—C(O)R), alkoxycarbonyl (—OCOR), amino, carbamoyl(—NHCOOR or —OCONHR), urea (—NHCONHR), thiol, (—SH), sulfoxy, sulfonyl, aryl, heteroaryl, and heterocycloalkyl.

The term "alkenyl" herein alone or as part of another group refers to a hydrocarbon radical straight, branched or cyclic containing from 2 to 12 carbon atoms and at least one carbon to carbon double bond. An alkenyl group may be optionally substituted in the same manner as described for an alkyl group.

The term "alkynyl" herein alone or as part of another group refers to a hydrocarbon radical straight, branched or cyclic containing from 2 to 12 carbon atoms and at least one carbon to carbon triple bond. An alkynyl group may be optionally substituted in the same manner as described for an alkyl group.

The term "alkoxy" as used alone or in combination herein refers to a straight or branched chain alkyl group covalently bonded to the parent molecule through an oxygen atom linkage containing from one to ten carbon atoms and the terms "$C_{1-6}$ alkoxy" and "lower alkoxy" refer to such groups containing from one to six carbon atoms. Examples include, but are not limited to, methoxy, ethoxy, propoxy, isopropoxy, butoxy, t-butoxy and the like. The term "optionally substituted" when used in connection with an alkoxy substituent refers to the replacement of up to two hydrogens, preferably on different carbon atoms with a radical selected from the group of lower alkyl, phenyl, cyano, halo, trifluoromethyl, nitro, hydroxy, alkanoyl, amino, monoalkyl amino and dialkylamino. Alkoxy groups may be substituted in the same manner that alkyl groups can be substituted as described above.

The term "sulfoxy" herein alone or as part of a group refers to —SO and may be substituted with, for example, alkyl, aryl or heteroaryl groups.

The term "sulfonyl" herein alone or as part of a group refers to —$SO_2$ and may be substituted with alkyl, aryl or heteroaryl groups.

The term "amino" herein alone or as part of another group refers to —$NH_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. Preferred substituents include alkylamino and dialkylamino, such as methylamino, ethylamino, dimethylamino, and diethylamino. These substituents may be further substituted with a carboxylic acid or any of the alkyl or aryl substituents set out herein. In addition, the amino substituents may be taken together with the nitrogen atom to which they are attached to form 1-pyrrolidinyl, 1-piperidinyl, 1-azepinyl, 4-morpholinyl, 4-thiamorpholinyl, 4-sulfoxymorpholine, 4-sulfonylmorpholine, 1-piperazinyl, 4-alkyl-1-piperazinyl, 4-arylalkyl-1-piperazinyl, 4-diarylalkyl-1-piperazinyl, 1-homopiperazinyl, 4-alkyl-1-homopiperazinyl, 4-arylalkyl-1-homopiperazinyl, 4-diarylalkyl-1-homopiperazinyl; 1-pyrrolidinyl, 1-piperidinyl, or 1-azepinyl, optionally substituted with alkyl, alkoxy, alkylthio, halo, trifluoromethyl or hydroxy.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkenyl, alkynyl, alkoxy, hydroxy, carboxy, carbamoyl, alkyloxycarbonyl, alkylaminocarbonyl, nitro, trifluoromethyl, amino, cycloalkyl, cyano, alkyl $S(O)_m$ (m=0, 1, 2), or thiol. Aryl groups may also be substituted with heterocycloalkyl and heterocycloaryl groups to form fused rings, such as dihydrobenzfuranyl, oxindolyl, indolyl, indolinyl, oxindolyl, benzoxazolidinonyl, benzoxazolinyl and benzoxazolidinone.

The term "cycloalkyl" herein alone or as part of another group refers to fully saturated and partially unsaturated hydrocarbon rings of 3 to 9, preferably 3 to 7 carbon atoms. Further, a cycloalkyl may be substituted. A substituted cycloalkyl refers to such rings having one, two, or three substituents, preferably one, selected from the group consisting of halo, alkyl, substituted alkyl, alkenyl, alkynyl, nitro, cyano, oxo (=O), hydroxy, alkoxy, thioalkyl, —$CO_2R$, —OC(=O)R, wherein R is H, alkyl, alkoxyalkyl, =N—OH, =N—O-alkyl, aryl, heteroaryl, heterocyclo, a five or six membered ketal (i.e. 1,3-dioxolane or 1,3-dioxane), —NR'R", —C(=O)NR'R", —OC(=O)NR'R", —NR'$CO_2$R", —NR'C(=O)R", —$SO_2$NR'R", and —NR'$SO_2$R", wherein each of R' and R" is independently selected from hydrogen, alkyl, substituted alkyl, and cycloalkyl, or R' and R" together form a heterocyclo or heteroaryl ring. Cycloalkyl groups may also be substituted with heteroatoms such as O, N, and S to form heterocycloalkyl groups. Preferred heterocycloalkyl groups include optionally substituted morpholine, homomorpholine (7 membered ring), thiomorpholine, piperazine, homopiperazine (7 membered ring), and piperidine, wherein the substituents are as defined above.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, nitro, cyano, hydroxy, alkoxy, thioalkyl, —$CO_2$H, —OC(=O)H, —$CO_2$-alkyl, —OC(=O)alkyl, phenyl, benzyl, phenylethyl, phenyloxy, phenylthio, cycloalkyl, substituted cycloalkyl, heterocyclo, heteroaryl, —NR'R", —C(=O)NR'R", —OC(=O)NR'R", —NR'$CO_2$R", —NR'C(=O)R", —$SO_2$NR'R", and —NR'$SO_2$R", wherein each of R' and R" is independently selected from hydrogen, alkyl, substituted alkyl, and cycloalkyl, or R' and R" together form a heterocyclo or heteroaryl ring.

Exemplary monocyclic heteroaryl groups include pyrrolyl, pyrrolidinyl, imidazolinyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, and the like. Preferred heteroaryl groups include substituted imidazoles.

Exemplary bicyclic heteroaryl groups include indolyl, indolinyl, oxindolyl, benzoxazolidinone, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

The term "halogen" or "halo" herein alone or as part of another group refers to chlorine, bromine, fluorine or iodine selected on an independent basis.

The term "hydroxy" herein alone or as part of another group refers to —OH.

The term "thioalkoxy" herein alone or as part of another group refers to an alkyl group as defined herein attached to the parent molecular group through a sulfur atom. Examples of thioalkoxy include, but are not limited to, thiomethoxy, thioethoxy, and the like.

Abbreviations: "Ph" represents phenyl; "Me" represents methyl; and "Et" represents ethyl.

The phrase "therapeutically effective amount" is intended to mean the amount of active compound or pharmaceutical agent that elicits the biological or medicinal response in a tissue, system, animal or human that is being sought by a researcher, veterinarian, medical doctor or other clinician.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the present invention may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of the present invention are employed. (For purposes of this application, topical application shall include mouth washes and gargles.)

The compounds of the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The compounds When a compound according to this invention is administered into a human subject, the daily dosage will normally be determined by the prescribing physician with the dosage generally varying according to the age, weight, sex and response of the individual patient, as well as the severity of the patient's symptoms.

An "anti-cancer agent" as used herein includes known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as irinotecan or topotecan; tubulin interacting agents, such as paclitaxel, docetaxel or the epothilones; hormonal agents, such as tamoxifen; thymidilate synthase inhibitors, such as 5-fluorouracil; UFT alone or in combination with leucovorin; anti-metabolites, such as methotrexate; tyrosine kinase inhibitors such as Iressa and Tarceva; angiogenesis inhibitors; EGF inhibitors; Eg5 inhibitors; VEGF inhibitors; CDK inhibitors; Her1/2 inhibitors and monoclonal antibodies directed against growth factor receptors such as erbitux (EGF), herceptin (Her2), or avastin (VEGF).

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

When $C_{1-6}$ alkyl, alkenyl, alkynyl, cycloalkyl are substituted, they are preferably substituted with one or more hydroxy, cyano, carbamoyl, hydroxy, alkoxy, thiol, alkenyl, thioalkoxy, amino, alkylamino, amido, sulfonyl, sulfoxy, sulfonamido, halo, heterocycloalkyl, aryl or heteroaryl.

When aryl or heteroaryl are substituted, they are preferably substituted with one or more alkyl, alkenyl, alkynyl, cyano, carbamoyl, hydroxy, alkoxy, thioalkoxy, amino, amido, sulfonamido, halo or with R', R" wherein R', R" form a ring that is fused to the aryl group. When $CH_2$aryl or heteroaryl are substituted, they are preferably substituted with one or more alkyl, alkenyl, alkynyl, cyano, carbamoyl, hydroxy, alkoxy, thioalkoxy, amino, amido, sulfonamido, or halogen.

When NH-Z-aryl or NH-Z-heteroaryl groups are substituted, they are preferably substituted with one or more alkyl, alkenyl, alkynyl, hydroxy, alkoxy, thioalkoxy, amino, halogen, nitro, nitrile, carboxylate, alkoxycarbonyl, carbamoyl, ester, amide, aryl, or heteroaryl groups.

The term "alkyl-$R^{25}$" includes optionally substituted alkyl groups such as methyl, ethyl, propyl, and butyl, attached to an $R^{25}$ group. $R^{25}$ generally includes hydrogen, alkenyl, hydroxy, thiol, alkoxy, thioalkoxy, amino, alkylamino, dialkylamino, aryl, heteroaryl, cyano, halo, sulfoxy, sulfonyl, —NHCOOH, —NHC(O)—, —NHSO$_2$—, —C(O)NH$_2$, heteroaryl or heterocycloalkyl groups such as morpholinyl or a group having the formula:

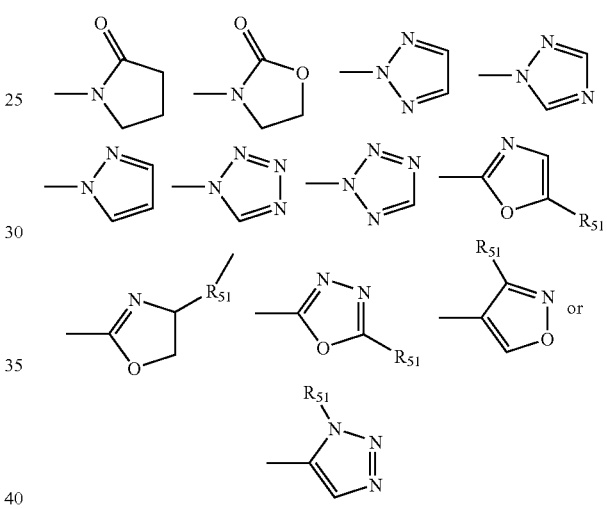

wherein $R_{51}$ is H or alkyl.

The terms "imidazole" and "imidazoline" herein alone or as part of another group includes substituted imidazoles and substituted imidazolines. Similarly, the term "tetrahydropyrimidine" includes substituted tetrahydropyrimidines. Likewise, the terms "piperazine", "piperidine" "morpholines", "homopiperazines", "homomorpholines" and "pyrrolidine" include substituted piperazines, substituted piperidines, substituted morpholines, substituted homomorpholines and substituted pyrrolidines, respectively. Preferred substituents include all those mentioned heretofore for heterocycloalkyl and heteroaryl groups.

The present invention is directed to compounds having the formula:

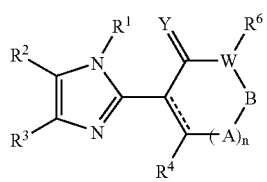

their enantiomers, diastereomers, pharmaceutically acceptable salts, hydrates, or esters thereof wherein the radicals are as defined previously.

Certain compounds of formula I may generally be prepared according to the following schemes and the knowledge of one skilled in the art. Solvates (e.g., hydrates) of the compounds of formula I are also within the scope of the present invention. Methods of solvation are generally known in the art. Accordingly, the compounds of the instant invention may be in the free or hydrate form, and may be obtained by methods exemplified by the following schemes below.

More specifically, Schemes I-IV illustrate the preparation of compounds claimed in this invention. The examples, which follow, illustrate the compounds that can be synthesized by these schemes. The schemes are not limited by the examples listed or by any substituents employed for illustrative purposes.

Scheme I describes the preparation of the imidazoles. The starting keto-oximes 1 are readily available using literature methods, e.g. Touster, O. *Organic reactions* (1967), 7:327-377. The keto-oxime is then heated with an aldehyde 2 and ammonium acetate in acetic acid to provide the imidazole 3 following reduction of the N-hydroxy imidazole. Aldehydes such as 2 are readily available from the commercially available substituted pyrimidines via metalation. A number of reagents are used for reducing the N-hydroxy imidazoles preferably $TiCl_3$ with HCl in methanol. The chloro group of imidazole 3 can be displaced with various nucleophiles such as amines, alcohols or sulfides. For illustration an amine is illustrated in Scheme I to provide compound 4.

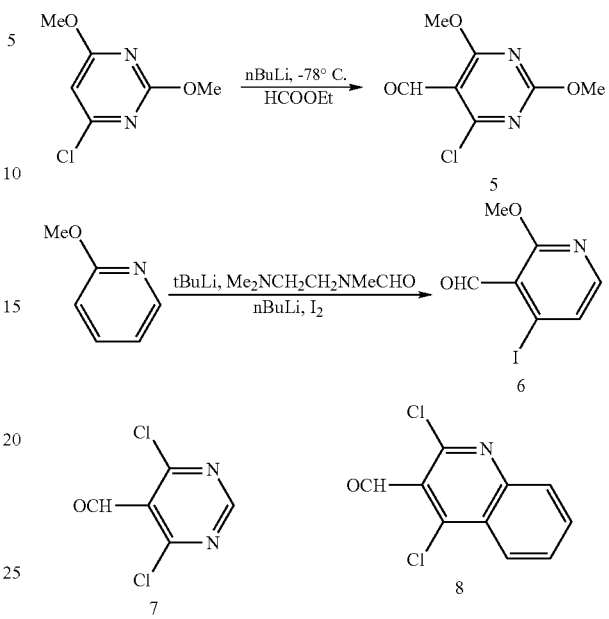

Scheme III illustrates the use of tricarbonyl compounds such as 9 for imidazole ring formation. Commercially avail-

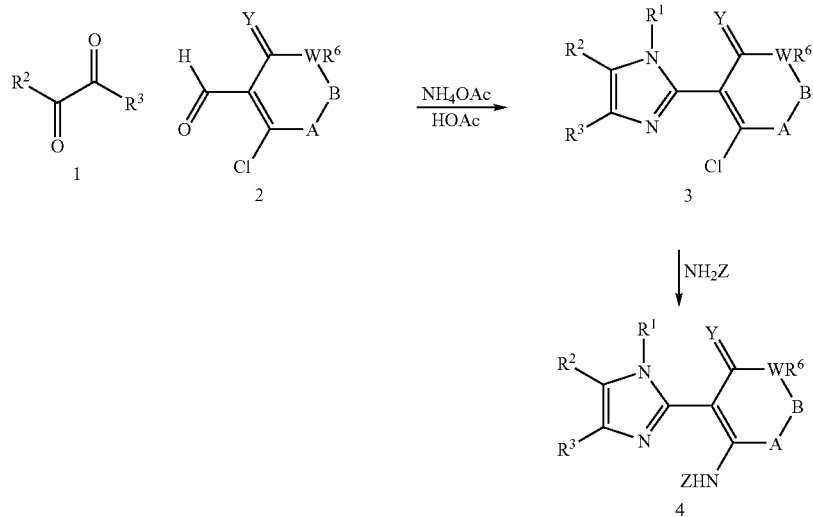

Scheme II illustrates the specific synthesis of two such aldehydes 5 and 6. Known aldehydes 7 (Gomtsyan, A.; Didomenico, S.; Lee, C.-H.; Matulenko, M. A.; Kim, K.; Kowaluk, E. A.; Wismer, C. T.; Mikusa, J.; Yu, H.; Kohlhaas, K.; Jarvis, M. F.; Bhagwat, S. S.; *J. Med. Chem.* (2002) 45 (17) 3639-3648) and 8 (Ashok, K.; Sridevi, G.; Umadevi, Y.; *Synthesis* (1993) 6: 623-626) could also be used. The substituted pyrimidine and pyridines can be metalated at low temperature using an alkyl lithium base and then formylated using a number of formylating reagents such as formyl imidazole, ethyl formate, DMF, or N-formyl-N,N',N"-trimethylethylenediamine.

able tricarbonyl ester 9 is reacted with aldehyde 2 in the presence of ammonium acetate and acetic acid. The resulting imidazole ester 10 could serve as a precursor to amides 11 via acid hydrolysis followed by amide formation using any number of dehydrating agents such as DCC, EDCI etc. Alternatively the ester group of 10 could be reduced to aldehyde 12 directly using DiBAl—H or reduced to the alcohol by any number of hydride reagents known to those skilled in the art and then reoxidized to the aldehyde by any number of oxidants known in the art. The aldehyde 12 could serve as a useful precursor for reductive amination to provide amines 13.

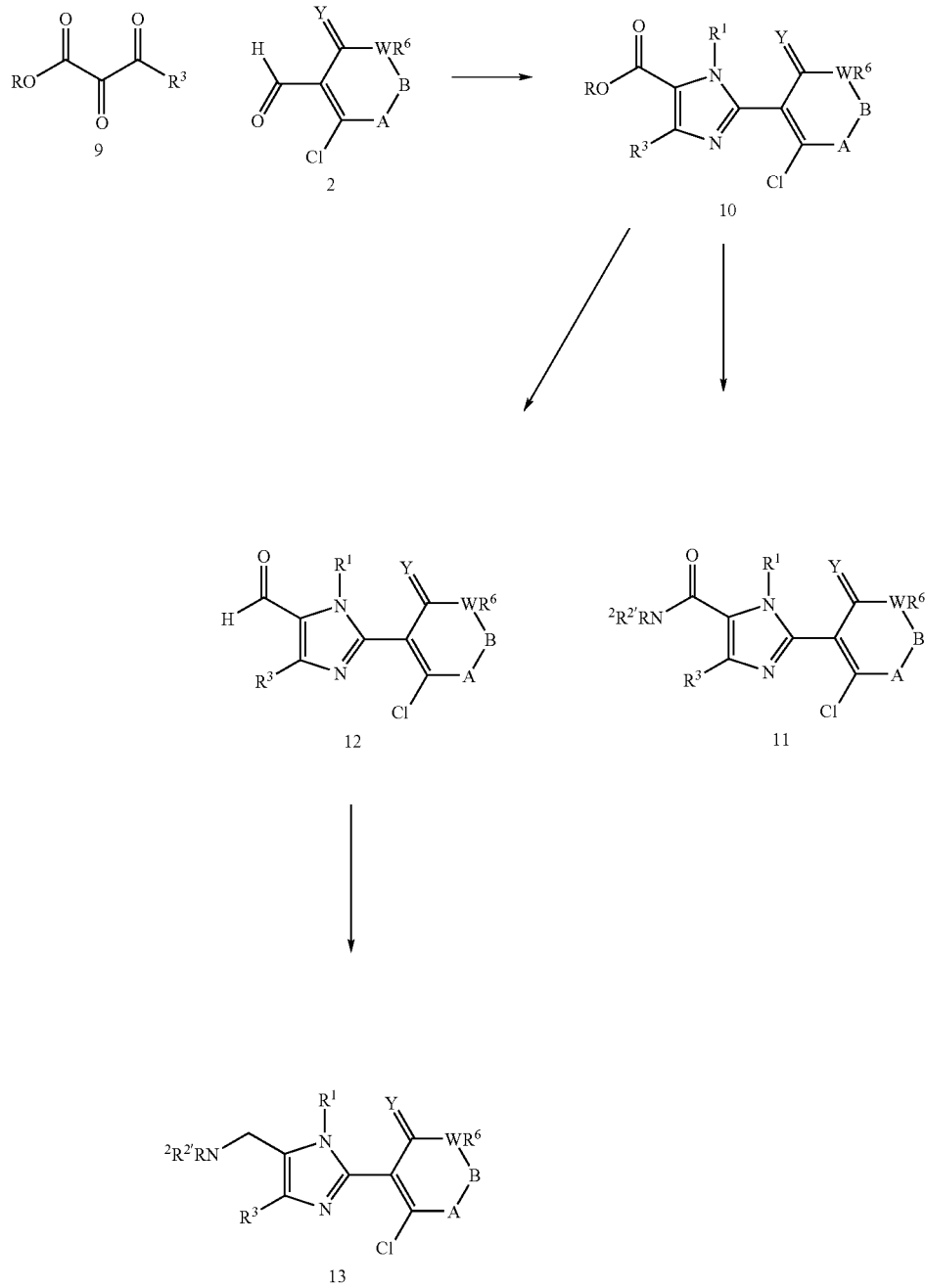

Scheme IV illustrates further transformation of imidazoles that bear a halogen atom using palladium catalysis using the general conditions developed by Suzuki [Yang et al. *Acta Chem. Scand.* (1993) 221; Suzuki et at. *Synth. Commun.* (1981) 11: 513] or Buchwald/Hartwig [Buchwald et al. *J Am. Chem. Soc.* (1994) 116: 7901; Hartwig et al. *J Am. Chem. Soc.* (1994) 116: 5969; Hartwig. *Angew. Chem., Int. Ed. Engl.* (1998) 37: 2046] and variations of these methods. Preparation of a bromide substituted imidazole 14 provides a substrate for Suzuki coupling with aryl, vinyl, and heterocyclic boronic acids to provide benzimidazoles 15. Likewise, amines and heterocycles such as piperazine or morpholine derivatives 16 can be prepared from the same bromide using amines under conditions described by Buchwald and Hartwig or variations thereof.

SCHEME IV

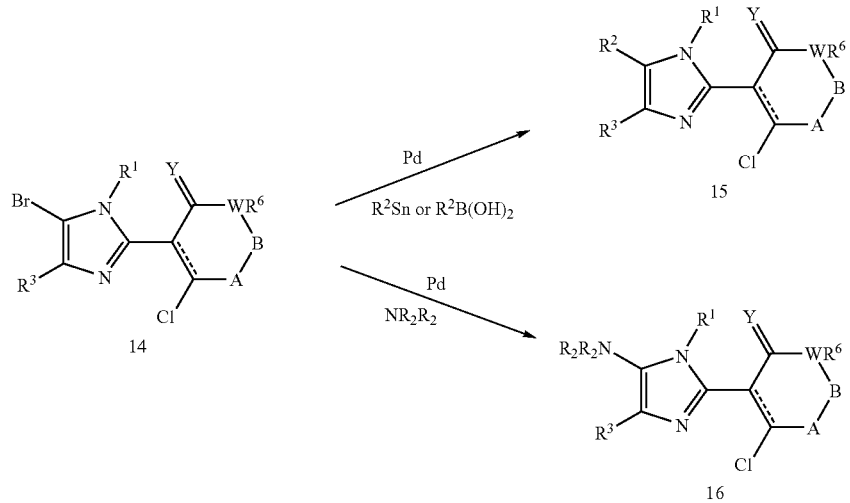

INTERMEDIATES AND EXAMPLES

A) Synthesis of amines

General Procedure for the Preparation of
2-Hydroxy-2-(substituted-phenyl)-ethylamines

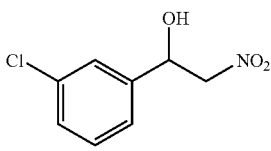

1-(3-Chloro-phenyl)-2-nitro-ethanol: To a solution of 3-chloro-benzaldehyde (20 g, 0.142 mol) in nitromethane (100 mL) were added magnesium sulfate (37.6 g, 0.312 mol) and phosphazene base $P_1$-t-bu-tris(tetramethylene) (4.43 g, 0.014 mol). The reaction mixture was stirred at room temperature for 2 h. After concentration in vacuo, the residue was purified by flash chromatography (25% EtOAc/hexane) to yield the title compound (26.4 g, 100%) as a green-yellow oil. $^1$H NMR (300 MHz, DMSO-$d_6$) δ 7.53 (1H, s), 7.35-7.42 (3H, m), 6.23 (1H, broad s), 5.32-5.33 (1H, m), 4.90 (1H, dd, J=3.2, 12.4 Hz), 4.60 (1H, dd, J=1.2, 12.4 Hz).

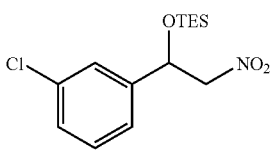

[1-(3-Chloro-phenyl)-2-nitro-ethoxy]-triethyl-silane: To a solution of 1-(3-chloro-phenyl)-2-nitro-ethanol (26 g, 0.14 mol) in DMF (50 mL) were added imidazole (28.6 g, 0.42 mol) and chlorotriethylsilane (25.3 g, 0.17 mol). The reaction mixture was stirred at room temperature for 2 h. After quenching with water, the mixture was extracted with ethyl acetate. The combined organic layers were washed with water and brine, dried over $Na_2SO_4$, and filtered. After removal of solvent, the crude product was purified by flash chromatography (2% EtOAc/hexane) to yield the title compound (37 g, 91%) as a colorless oil. $^1$H NMR (300 MHz, CDCl$_3$) δ 7.40 (1H, s), 7.27-7.32 (3H, m), 5.40 (1H, dd, J=3.2, 9.5 Hz), 4.51 (1H, dd, J=9.5, 12.1 Hz), 4.36 (1H, dd, J=3.3, 12.1 Hz), 0.85 (9H, t, J=7.5 Hz), 0.54 (6H, q, J=7.5 Hz).

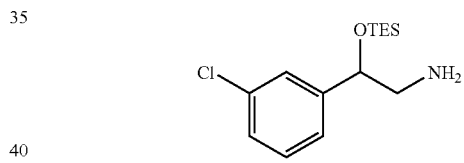

2-(3-Chloro-phenyl)-2-triethylsilanyloxy-ethylamine: Raney nickel (1 g) was washed with distilled water five times and methanol three times. [1-(3-Chloro-phenyl)-2-nitro-ethoxy]-triethyl-silane (10 g, 0.032 mol) and Raney nickel in methanol (100 mL) was hydrogenated (35 psi) at room temperature for 14 h. The reaction mixture was filtered through a pad of celite and rinsed with methanol. Concentration of the filtrate to dryness gave the title compound (5.6 g, 62%) as a colorless oil which was used for the next step without purification. $^1$H NMR (300 MHz, CDCl$_3$) δ 7.32 (1H, s), 7.18-7.26 (3H, m), 4.70 (1H, t, J=5.8 Hz), 2.86 (2H, m), 0.89 (9H, t, J=7.9 Hz), 0.56 (6H, q, J=7.8 Hz). LRMS (M+H)$^+$ m/z 286.

General Procedure for the Preparation of
2-Hydroxy-2-(substituted-phenyl)-ethylamines

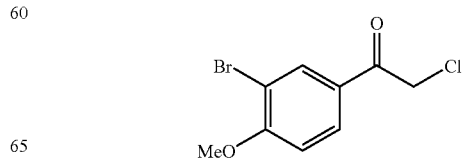

4-methoxy-3-bromophenyl chloroacetophenone: To a suspension of AlCl$_3$ (13.4 g, 0.10 mol) in methylene chloride (40 mL) was added a solution of 2-bromoanisole (12.5 mL, 0.10 mol) and chloroacetyl chloride (8 mL, 0.10 mol) at 0° C. The solution was warmed to ambient temperature for two hours and poured onto ice and extracted with methylene chloride, washed with saturated sodium bicarbonate solution, brine, and dried over MgSO$_4$. The solution was filtered, concentrated and crystalized from EtOH to give 15.37 g of white solid. LRMS [M−H]−260.8; IR (KBr) 1697, 1048, 1255 cm$^{-1}$; $^1$HNMR (300 MHz, CDCl$_3$) δ 8.18 (s, 1H), 7.94 (dd, J=8.67 Hz, 1H), 6.96 (d, J=8.67 Hz, 1H), 4.62 (s, 2H), 3.98 (s, 3H); $^{13}$C NMR (CDCl$_3$, 75.5 Hz) δ 188.8, 160.3, 134.1, 129.9, 128.2, 112.4, 111.3, 56.6, 45.3.

General Procedure for Chiral Reduction of Chloroketones and Ammonolysis

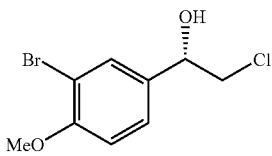

(S)-1-[4-methoxy-3-bromophenyl]-2-chloro ethanol: To a solution of (S)-Methyl-CBS-oxazaborolidine (1M in toluene, 0.745 mL, 0.745 mmol) and BH$_3$-THF (8 mL, 8 mmol) was added at the same time a solution of BH$_3$-THF (19 mL, 19 mmol) and a solution of the chloroketone (10.03 g, 37.98 mmol) in 19 mL of THF. Both solutions were added dropwise over 30 minutes. The solution was stirred for 1 hour and quenched with the slow addition of methanol (50 mL). The solution was concentrated and the residue chromatographed over a short silica gel column (1:1 hexane/ethyl acetate) to give a quantitative yield (10.0 g) of chlorohydrin as a clear oil. IR (KBr) 1053, 1258, 3406 cm$^{-1}$; $^1$H NMR (300 MHz, CDCl$_3$) δ 7.59 (s, 1H), 7.30 (dd, J=2.16 Hz, 1H), 6.90 (d, J=8.46 Hz, 1H), 4.83 (dd, J=3.57 Hz, 1H), 3.90 (s, 3H), 3.64 (ddd, J=3.6, 11.1, 8.7, 2H), 2.04 (b s, 1H). $^{13}$C NMR(CDCl$_3$, 75.5 MHz) δ 155.9, 133.5, 131.1, 126.3, 111.9, 73.1, 60.4, 56.3, 50.7.

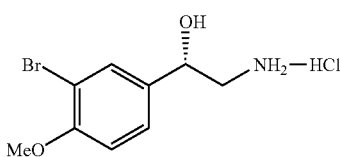

(S) 2-Amino-1-[3-bromo-4-methoxyphenyl]ethanol Hydrochloride: To a solution of the chlorohydrin (10.0 g, 37.9 mmol) in 120 mL of methanol at −40° C. was added 100 grams of ammonia. The solution was sealed in a pressure bottle and warmed to ambient temperature and stirred for 48 hours. The solution was cooled and opened. The ammonia was allowed to evaporate and solution concentrated. The residue was crystalized from ethanol/ethyl acetate to give 3.83 g of white solid (35%). The material was reacted with Boc$_2$O in ethyl acetate and saturated sodium bicarbonate and analyzed by chiral HPLC using a chiralcel OJ column using 95% hexane/ethanol as elutant and determined to by 98% ee. Additional crops of 2.96 and 1.41 g were collected for a total of 75% yield. LRMS [M+H]+246; IR (cm$^{-1}$, KBr) 1055, 1261, 3001, 2948, 3356; $^1$H NMR (500 MHz, DMSO) δ 8.09 (b s, 2H), 7.58 (s, 1H), 7.36 (dd, J=2.05, 6.45 Hz, 1H), 7.11 (d, J=8.5 Hz, 1H) 6.10 (s, 1H), 4.80 (m, 1H), 3.84 (s, 3H), 3.00 (ddd, J=2.7, 12.6, 9.5 Hz, 2H); $^{13}$C NMR (DMSO, 75.5 MHz) δ 154.8, 135.4, 130.4, 126.6, 112.4, 110.4, 67.9, 56.2, 45.4.

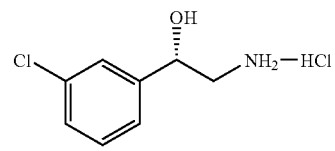

(S) 2-Amino-1-[3-chlorophenyl]ethanol Hydrochloride: was prepared according to the general procedure outlined above. LRMS [M+H]+172; IR (KBr, cm−1) 3048, 3351, 2952; $^1$H NMR (300 MHz, MeOD) δ 7.48 (s, 1H), 7.35 (m, 3H), 3.31 (ddd, J=1.5, 3.12, 9.15 Hz 2H).

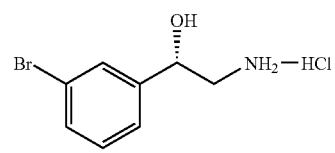

(S)-2-Amino-1-[3-bromophenyl]ethanol Hydrochloride: was prepared according to the general procedure outlined above. LRMS [MH]+217.9; IR (KBr, cm−1) 3025, 3443, 2891; $^1$H NMR (500 MHz, DMSO) δ 7.93 (b s, 2H), 7.60 (s, 1H), 7.52 (d, 1H), 7.41 (s, 1H), 7.35 (d, J=7.7 Hz, 1H) 6.17 (s, 1H), 4.82 (m, 1H), 3.08 (ddd, J=2.6, 12.7, 9.6 Hz, 2H); $^{13}$C NMR (DMSO, 75.5 MHz) δ 144.4, 130.5, 128.7, 125.0, 121.6, 68.3, 45.1.

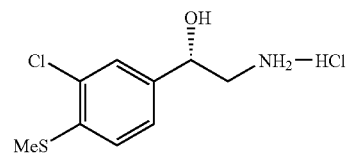

(S)-2-Amino-1-[3-chloro-4-methylthiophenyl]ethanol Hydrochloride: was prepared according to the general procedure outlined above. LRMS [M+H]+217.9; IR (KBr, cm−1) 3007, 3358; $^1$H NMR (500 MHz, DMSO) δ 8.12 (b s, 2H), 7.46 (s, 1H), 7.37 (s, 1H), 7.35 (d, 1H) 6.19 (d, 1H), 4.83 (m, 1H), 3.01 (ddd, J=3.2, 12.8, 9.3 Hz, 2H); $^{13}$C NMR (DMSO, 75.5 MHz) δ 139.6, 136.5, 129.8, 126.6, 125.4, 68.0, 45.2, 14.2.

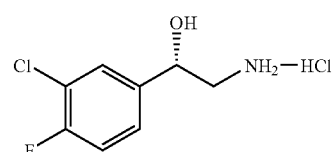

(S)-2-Amino-1-[3-chloro-4-fluoro-phenyl]ethanol Hydrochloride: was prepared according to the general procedure outlined above. LRMS [M+H]+189.9; IR (KBr, cm−1) 1509, 3008, 3359; $^1$H NMR (500 MHz, DMSO) δ 8.21 (b s, 2H), 7.61 (d, 15 J=7.85 Hz, 1H), 7.42 (m, 2H), 6.29 (s, 1H), 4.88

(m, 1H), 3.03 (ddd, J=3.4, 12.8, 9.2 Hz, 2H); $^{13}$CNMR (DMSO, 75.5 MHz) δ 157.5, 155.5, 139.7, 128.1, 126.7, 119.3, 116.7, 109.0, 67.8, 45.2.

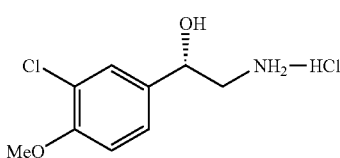

(S)-2-Amino-1-[3-chloro-4-methoxyphenyl]ethanol Hydrochloride: was prepared according to the general procedure outlined above. LRMS [M+H]+202; IR (KBr, cm−1) 3354, 3003, 2949, 1288, 1064; $^1$H NMR (500 MHz, DMSO) δ 8.18 (brs, 3H), 7.43 (d, J=2.0 Hz, 1H), 7.31 (dd, J=8.5, 2.0 Hz, 1H), 7.14 (d, J=5.1 Hz, 1H), 6.11 (s, 25 1H), 4.81 (m, 1H), 3.84 (s, 3H), 2.99 (dd, J=13, 3.5 Hz, 1H), 2.83 (dd, J=12.5, 9 Hz, 1H); $^{13}$C NMR (DMSO, 125 MHz) δ 153.9, 135.0, 127.3, 125.8, 120.8, 112.6, 68.0, 56.1, 45.5; Elemental Analysis Calcd for $C_9H_{12}ClNO_2$—HCl: C, 45.39; H, 5.50; N, 5.88. Found: C, 45.38; H, 5.43; N, 5.70.

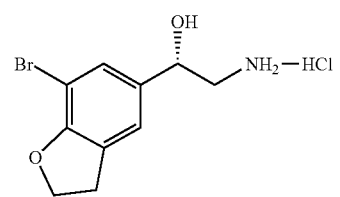

(S)-2-Amino-1-(7-bromo-2,3-dihydrobenzfuran-5-yl)-2-aminoethanol Hydrochloride: was prepared according to the general procedure outlined above. LRMS [M+H]+258; IR (KBr, cm−1) 3349, 3006, 2928, 1485, 1045, 983; $^1$H NMR (500 MHz, DMSO) δ 8.13 (brs, 3H), 7.29 (s, 1H), 7.23 (s, 1H), 6.08 (d, J=4 Hz, 1H), 4.76 (m, 1H), 4.61 (t, J=9 Hz, 2H), 3.29 (t, J=9 Hz, 2H), 2.96 (dd, J=13, 3.5 Hz, 1H), 2.82 (dd, J=13, 9.5 Hz, 1H); $^{13}$C NMR (DMSO, 125 MHz) δ 156.3, 135.9, 129.1, 128.1, 122.1, 100.9, 71.5, 68.2, 45.6, 29.9; Elemental Analysis Calcd for $C_{10}H_{12}BrNO_2$—HCl: C, 40.77; H, 4.44; N, 4.75. Found: C, 40.77; H, 4.63; N, 4.63.

General Procedure for the Preparation of 2-Amino-3-substituted-phenyl)-propanol

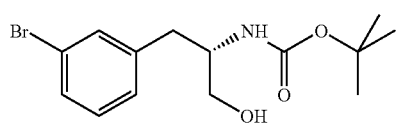

(S)-(2-(3-Bromo-phenyl)-1-hydroxymethyl-ethyl]-carbamic acid tert-butyl ester: To a solution of (S)-3-(3-bromo-phenyl)-2-tert-butoxycarbonylamino-propinic acid (500 mg, 1.45 mmol) in THF (30 mL) was added borane-tetrahydrofuran complex (1.0 M solution) (4.35 mL, 4.35 mmol). The reaction mixture was stirred at room temperature for 14 h and quenched with acetic acid (1 mL). After removal of most solvent, the residue was extracted with EtOAc, washed with brine, dried over $Na_2SO_4$. After concentration, the crude product (400 mg, 83%) was used the preparation of (S)-2-Amino-3-(3-bromo-phenyl)-propan-1-ol without purification. LCMS (M+H)$^+$ m/z 330 (t=1.61 min

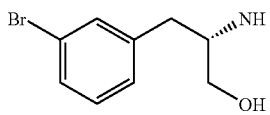

(S)-2-Amino-3-(3-bromo-phenyl)-propan-1-ol: To a solution of (S)-[2-(3-bromo-phenyl)-1-hydroxymethyl-ethyl]-carbamic acid tert-butyl ester (400 mg, 1.21 mmol) in methanol (30 mL) was added 4 M HCl in dioxane (2 mL, excess). The reaction mixture was stirred at room temperature for 14 h. After concentration in vacuo, the residue was used for the next step without purification. LCMS (M+H)$^+$ m/z 230 (t=0.78 min.)

B) Synthesis of Aldehydes

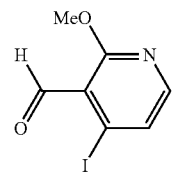

4-Iodo-2-methoxy-pyridine-3-carbaldehyde (WO 95/29917): A 5-liter three-necked round flask was equipped with an overhead mechanical stirrer under nitrogen, the flask was charged with THF (1 L) and cooled to −78° C. To this stirred solution was added tert-butyllithium (1.7 M solution in pentane) (800 mL, 1.36 mol) via canula followed by 2-methoxypyridine (132.2 g, 1.21 mol) at −78° C. The mixture was stirred for 1 h at −78° C. To the mixture was added N-formyl-N,N',N'-trimethylethylenediamine (176 mL, 1.37 mol) dropwise at −78° C. The reaction mixture was stirred for ca. 30 min at −78° C. before warming to −23° C. over ca. 30 min. To the mixture at −23° C. was added ethylene glycol dimethyl ether (1 L) followed by n-butyllithium (2.5 M solution in hexane) (800 mL, 2.0 mol). The resulting mixture was stirred for ca. 2 h during which time the reaction mixture turned deep green. A 12-L 4-necked round flask was charged with iodine (571 g, 2.25 mol) and ethylene glycol dimethyl ether (2 L) and the resultant solution was cooled to −78° C. The contents of the 5-L flask were transferred via canula to the mixture of iodine and ethylene glycol dimethyl ether in the 12-L flask at −78° C. After the addition was complete, the reaction mixture was stirred for an additional 1 h at −78° C. The cooling bath was removed and the mixture was allowed to warm to about 0° C. and treated with 2 L of water and 2 L of 1 N hydrochloric acid. Methyl t-butyl ether (2 L) was added and the layers were separated. The aqueous layer was extracted with 2×1 L of methyl t-butyl ether. The combined organic layers were washed with saturated $Na_2S_2O_3$ (1.2 L), brine (1.2 L), dried over $Na_2SO_4$. After concentration in vacuo, the thick slurry was diluted with hexane (1 L). The mixture was cooled with an ice/water bath for ca. 30 min. The precipitate was filtered and dried over vacuum to yield the title compound as a light yellow solid. $^1$H NMR (300 MHz, CDCl$_3$) δ 10.22 (s, 1H), 7.86 (1H, d, J=5.3 Hz), 7.54 (1H, d, J=5.3 Hz), 4.06 (3H, s). LCMS (M+H)$^+$ m/z 364 (t=2.26 min.).

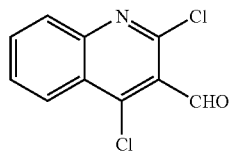

2,4-Dichloro-quinoline-3-carboxaldehyde: A stirred solution of 5.0 gm (25.3 mmol) of the 2,4-Dichloro quinoline was cooled to −78° C., to which was added dropwise a 14 mL (27.8 mml) of 2M solution of lithium diisopropylamide in tetrahydrofuran under nitrogen atmosphere, stirred for 30 min, and then was added 4.9 mL (65.3 mmol) of dimethylformamide. The reaction mixture was stirred at −78° C. for 3 hrs, allowed to warm to room temperature, quenched with saturated NH$_4$Cl solution, diluted with water, and extracted with ethyl acetate. The combined organic extract was washed with water, brine, and dried (Na$_2$SO$_4$), and the solvent was evaporated to furnish the residue which was chromatographed (10% ethyl acetate/hexanes) to afford the pure product. LRMS [M+H]+226; $^1$H NMR (400 MHz, CDCl$_3$) δ 10.63 (s, 1H), 8.39 (d, 1H, J=8.8 Hz), 8.06 (d, 1H, J=8.4 Hz), 7.92 (dd, 1H, J=8.4, 8.8 Hz), 7.75 (dd, 1H, J=8.8, 8.4 Hz).

C) Synthesis of Imidazole Intermediates

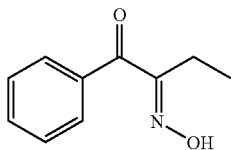

1-Phenyl-butane-1,2-dione 2-oxime: To a stirred solution of the butyrophenone (300 mg, 2.0 mmol) in tetrahydrofuran (8 mL) was added t-butyl nitrite (0.475 mL, 4.0 mmol) and hydrochloric acid (4N in dioxane, 0.65 mL, 2.6 mmol). The reaction was stirred at RT for 3 hours, then the solvent was evaporated and the residue was purified by Prep HPLC (ammonium acetate/water/acetonitrile) to give the title material (0.200 g, 56%). HPLC 91% (220 nm), LCMS (+ESI, M+H+) m/z 178; $^1$H NMR (400 MHz, methanol-d$_4$) δ (ppm): 1.13 (3H, t, J=7.6 Hz), 2.71 (2H, qa, J=7.6 Hz), 7.45 (2H, br t), 7.57 (1H, br t), 7.90 (2H, d, J=7.0 Hz).

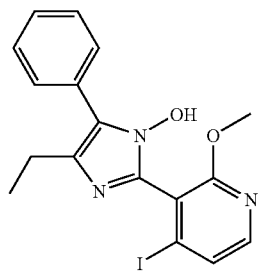

4-Ethyl-2-(4-iodo-2-methoxy-pyridin-3-yl)-5-phenyl-imidazol-1-ol: To a stirred solution of 1-phenyl-butane-1,2-dione 2-oxime (0.200 g, 1.13 mmol) in acetic acid (6 mL) was added 4-iodo-2-methoxy-pyridine-3-carbaldehyde (0.297 g, 1.13 mmol) followed by ammonium acetate (0.435 g, 5.65 mmol). The mixture was refluxed for 2 hours, then the solvent was evaporated and the residue was purified by Prep HPLC (ammonium acetate/water/acetonitrile) to give the title material (0.379 g, 80%). HPLC 98% (220 nm), LCMS (+ESI, M+H+) m/z 422; $^1$H NMR (400 MHz, methanol-d$_4$) δ (ppm): 1.34 (3H, t, J=7.6 Hz), 2.93 (2H, qa, J=7.6 Hz), 3.95 (3H, s) 7.41-7.43 (1H, m), 7.51 (2H, t, J=7.6 Hz), 7.63-7.59 (3H, m), 8.00 (1H, d, J=5.3 Hz).

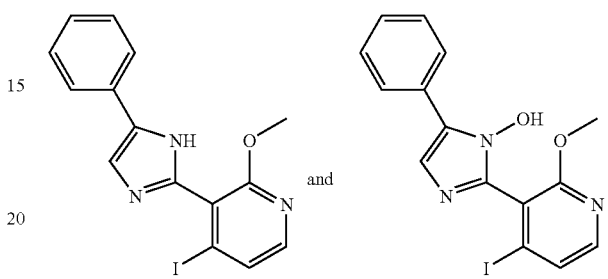

4-Iodo-2-methoxy-3-(5-phenyl-1H-imidazol-2-yl)-pyridine and 2-(4-iodo-2-methoxy-pyridin-3-yl)-5-phenyl-imidazol-1-ol: Isonitrosoacetophenone (0.030 g, 0.114 mmol) was reacted as described for the synthesis of 4-ethyl-2-(4-iodo-2-methoxy-pyridin-3-yl)-5-phenyl-imidazol-1-ol and gave 4-iodo-2-methoxy-3-(5-phenyl-1H-imidazol-2-yl)-pyridine (0.008 g, 19%) and 2-(4-iodo-2-methoxy-pyridin-3-yl)-5-phenyl-imidazol-1-ol (0.007 g, 16%). 4-Iodo-2-methoxy-3-(5-phenyl-1H-imidazol-2-yl)-pyridine: LCMS (+ESI, M+H+) m/z 378; $^1$H NMR (400 MHz, DMSO-d$_6$) δ (ppm): 3.83 (3H, s), 7.17-7.97 (8H, m), 12.29 and 12.60 (1H, 2 br s). 2-(4-Iodo-2-methoxy-pyridin-3-yl)-5-phenyl-imidazol-1-ol: : LCMS (+ESI, M+H+) m/z 378; $^1$H NMR (400 MHz, DMSO-d$_6$) δ (ppm): 3.82 and 3.92 (3H, 2 d), 7.19-8.05 (8H, m), 11.68 and 12.70 (1H, 2s).

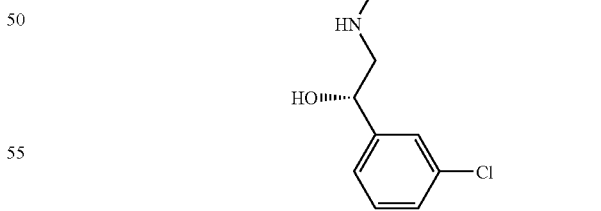

4-[2-(3-Chloro-phenyl)-2-hydroxy-ethylamino]-3-(1-hydroxy-5-phenyl-1H-imidazol-2-yl)-1H-pyridin-2-one: 2-(4-Iodo-2-methoxy-pyridin-3-yl)-5-phenyl-imidazol-1-ol (0.020 g, 0.053 mmol) was dissolved in N,N-dimethylformamide (4 mL) and treated with triethylamine (20 μL, 0.159 mmol) and the hydrochloric acid salt of (S)-2-amino-1-[3-chlorophenyl]ethanol (0.017 g, 0.0795 mmol). This mixture was heated at 65° C. for 3 hours, then the solvent was evaporated. The residue was purified by Prep HPLC (ammonium acetate/water/acetonitrile) to give the title material (0.006 g, 27%) as a beige solid. HPLC 87.9% (220 nm), LCMS (+ESI, M+H+) m/z 423; IR ν (cm−1): 2923, 2853, 1637; HRMS calcd for $C_{22}H_{20}N_4O_3Cl$ (M+H)+=423.1224, found: 423.1221; 1H NMR (400 MHz, methanol-$d_4$) δ (ppm): 3.56 (1H, dd, J=13.2 and 7.0 Hz), 3.69 (1H, dd, J=13.2 and 4.6 Hz), 4.96 (1H, m), 6.36 (1H, d, J=7.4 Hz), 7.22-7.79 (11H, m).

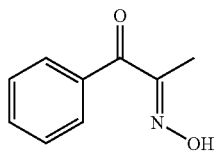

1-Phenyl-propane-1,2-dione 2-oxime: Propiophenone (0.100 g, 0.746 mmol) was reacted as described for the synthesis of 1-phenyl-butane-1,2-dione 2-oxime and gave the title material (0.103 g, 84%). HPLC 98.7% (220 nm), LCMS (+ESI, M+H+) m/z 279; 1H NMR (400 MHz, methanol-$d_4$) δ (ppm): 2.09 (3H, s), 7.42 (2H, m), 7.55 (1H, m), 7.89 (2H, d, J=7.1 Hz).

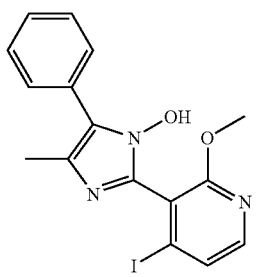

2-(4-Iodo-2-methoxy-pyridin-3-yl)-4-methyl-5-phenyl-imidazol-1-ol: 1-Phenyl-propane-1,2-dione 2-oxime (0.103 g, 0.631 mmol) was reacted as described for the synthesis of 4-ethyl-2-(4-iodo-2-methoxy-pyridin-3-yl)-5-phenyl-imidazol-1-ol and afforded the title material (0.093 g, 36%). LCMS (+ESI, M+H+) m/z 407.

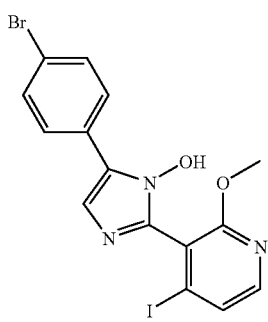

5-(4-Bromo-phenyl)-2-(4-iodo-2-methoxy-pyridin-3-yl)-imidazol-1-ol: (4-Bromo-phenyl)-oxo-acetaldehyde oxime (0.242 g, 1.06 mmol) was reacted as described for the synthesis of 4-ethyl-2-(4-iodo-2-methoxy-pyridin-3-yl)-5-phenyl-imidazol-1-ol and gave the title material (0.090 g, 18%). LCMS (+ESI, M+H+) m/z 472, 474.

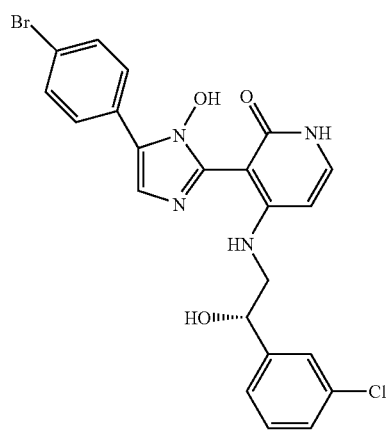

3-[5-(4-Bromo-phenyl)-1-hydroxy-1H-imidazol-2]-yl-4-[2-(3-chloro-phenyl)-2-hydroxy-ethylamino]-1H-pyridin-2-one: 5-(4-Bromo-phenyl)-2-(4-iodo-2-methoxy-pyridin-3-yl)-imidazol-1-ol (0.075 g, 0.159 mmol) was dissolved in acetic acid/concentrated hydrochloric acid (2 mL 2 mL) and the reaction was refluxed for 2 hours. The solvent was evaporated and the residue was dissolved in N,N-dimethylformamide (3 mL) and treated with triethylamine (excess) and the hydrochloric acid salt of (δ)-2-amino-1-[3-chlorophenyl]ethanol (0.066 g, 0.477 mmol). The mixture was heated at 80° C. for 5 hours. The reaction was then diluted in ethyl acetate, washed with water. The organic phase was dried over anhydrous magnesium sulfate, filtered and concentrated. The residue was purified by Prep HPLC (ammonium acetate/water/acetonitrile) to give the title material (0.015 g, 19%). LCMS (+ESI, M+H+) m/z 501, 503, (−ESI, M−H−) m/z 499, 501; 1H NMR (400 MHz, methanol-$d_4$) δ (ppm): 3.55 (1H, dd, J=13.3 and 7.3 Hz), 3.70 (1H, dd, J=13.3 and 4.3 Hz), 4.96 (1H, m), 6.35 (1H, d, J=7.7 Hz), 7.23-7.78 (10H, m).

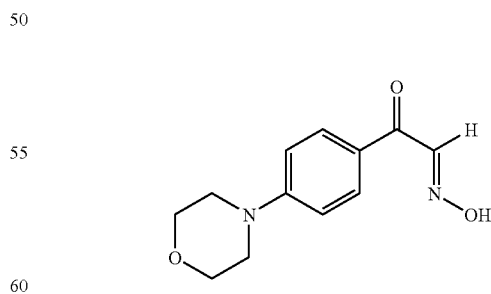

(4-Morpholin-4-yl-phenyl)-oxo-acetaldehyde oxime: 4-Morpholino-acetophenone (0.200 g, 0.974 mmol) was reacted as described for the synthesis of 1-phenyl-butane-1,2-dione 2-oxime and gave the title material (0.111 g, 49%).

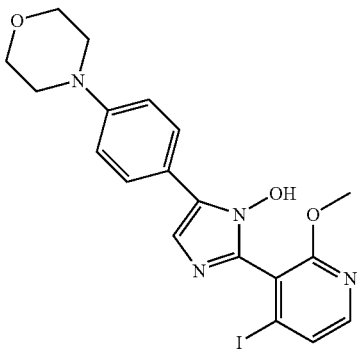

2-(4-Iodo-2-methoxy-pyridin-3-yl)-5-(4-morpholin-4-yl-phenyl)-imidazol-1-ol: (4-Morpholin-4-yl-phenyl)-oxo-acetaldehyde oxime (0.111 g, 0.474 mmol) was reacted as described for the synthesis of 4-ethyl-2-(4-iodo-2-methoxy-pyridin-3-yl)-5-phenyl-imidazol-1-ol and afforded the title material (0.049 g, 22%).

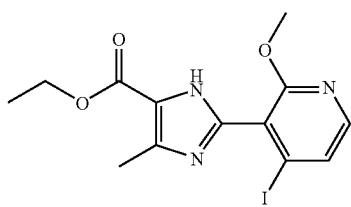

2-(4-Iodo-2-methoxy-pyridin-3-yl)-5-methyl-3H-imidazole-4-carboxylic acid ethyl ester: To a slurry of ammonium acetate (0.837 g, 10.9 mmol) in acetic acid (10 mL) was added 2,3-dioxo-butyric acid ethyl ester (0.176 g, 1.086 mmol) (*J. Org. Chem.*, 60 (25), p. 8231 (1995)) followed by 4-iodo-2-methoxy-pyridine-3-carbaldehyde (0.286 g, 1.086 mmol). The mixture was stirred at 65° C. for ~3 hours. The solution was cooled to room temperature and the solvent was evaporated. The residue was dissolved in ethyl acetate and washed with saturated sodium bicarbonate and brine. The organic phase was dried over anhydrous magnesium sulfate, filtered and concentrated. The residue was purified by silica gel column chromatography (ethyl acetate) to give the title material (0.199 g, 47%) as a yellow solid. LCMS (+ESI, M+H+) m/z 388; $^1$H NMR (400 MHz, methanol-d$_4$) δ (ppm)(mixture of tautomers): 1.27 and 1.29 (3H, 2t, J=7.1 Hz), 2.39 and 2.46 (3H, 2s), 3.77 and 3.79 (3H, 3s), 4.20 and 4.25 (2H, 2q, J=7.1 Hz), 7.56 and 7.58 (1H, 2d, J=5.6 and 5.3 Hz), 7.94 and 7.95 (1H, 2d, J=5.6 and 5.3 Hz), 12.58 and 12.82 (1H, 2s).

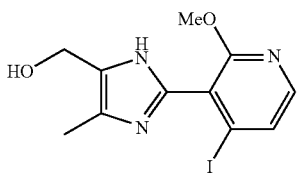

(2-(4-iodo-2-methoxypyridin-3-yl)-4-methyl-1H-imidazol-5-yl)methanol: To a stirred solution of 2-(4-iodo-2-methoxy-pyridin-3-yl)-5-methyl-3H-imidazole-4-carboxylic acid ethyl ester (0.109 g, 0.318 mmol) in dichloromethane (10 mL) was added diisobutylaluminum hydride (1.5 M in toluene, 1.06 mL, 1.59 mmol) at 0° C. The reactions was stirred at 0° C. for 1 hour then a saturated aqueous solution of ammonium chloride was added. The two phases were separated and the aqueous phase was extracted with dichloromethane (4×). The organic layers were dried over anhydrous magnesium sulfate, filtered and concentrated. The residue (80 mgs) was purified by Prep HPLC (ammonium acetate/acetonitrile/water) to give the title material (0.044 g, 40%) along with the starting material (0.028 g, 26%). $^1$H NMR (400 MHz, MeOH-d$_4$) δ (ppm): 2.22 (s, 4H) 3.77 (s, 4H) 4.49 (s, 3H) 7.45 (d, J=5.31 Hz, 1H) 7.77 (d, J=5.56 Hz, 1H).

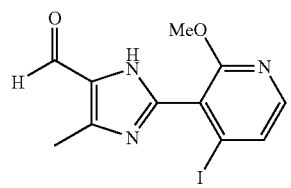

2-(4-iodo-2-methoxypyridin-3-yl)-4-methyl-1H-imidazole-5-carbaldehyde: To a stirred suspension of 3-(5-(hydroxymethyl)-4-methyl-1H-imidazol-2-yl)-4-iodopyridin-2(1H)-one (0.020 g, 0.0579 mmol) in dichloromethane (2 mL) was added the Dess-Martin reagent (0.049 g, 0.1158 mmol) at room temperature. The reaction became clear after 5 minutes of stirring. Ethyl acetate was added and the reaction was washed with 5% aqueous Na$_2$S$_2$O$_3$.5H$_2$O, saturated aqueous sodium bicarbonate and brine. The organic layer was driede over anhydrous magnesium sulfate, filtered and concentrated. The residue was purified on silica gel chromatography (ethyl acetate) to give the title material (0.009 g, 45%). $^1$H NMR (400 MHz, Acetone-d6) δ (ppm): 2.47 (s, 3H) 3.72 (s, 3H) 7.42-7.50 (m, 1H) 7.78 (s, 1H) 9.81 (s, 1H).

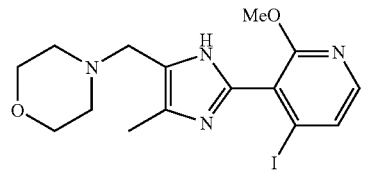

4-((2-(4-iodo-2-methoxypyridin-3-yl)-4-methyl-1H-imidazol-5-yl)methyl)morpholine: To a stirred solution of 2-(4-iodo-2-oxo-1,2-dihydropyridin-3-yl)-4-methyl-1H-imidazole-5-carbaldehyde (0.008 g, 0.0233 mmol) in methanol (2 mL and acetic acid (50 μL) was added morpholine (6 μL, 0.070 mmol) followed by sodium cyanoborohydride (1 mg (0.016 mmol). The mixture was stirred at room temperature for 2 hours then at 0° C. overnight. Morpholine (12 μL, 0.014 mmol) and sodium cyanoborohydride (1 mg, 0.016 mmol) were added again and the reaction was stirred for 2 more hours at room temperature. The solvents were evaporated and the residue was purified on a C-18 cartridge and then on Prep HPLC (trifluoroacetic acid/water/acetonitrile) to give the title material (0.008 g, 83%). $^1$H NMR (400 MHz, MeOH-d4) δ (ppm): 2.61 (br s, 3H) 3.44 (br s, 3H) 4.04-4.14 (m, 8H) 4.46 (s, 2H) 7.80 (d, J=5.31 Hz, 1H) 8.15 (br d, 1H).

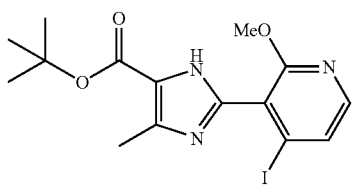

tert-Butyl 2-(4-iodo-2-methoxypyridin-3-yl)-4-methyl-1H-imidazole-5-carboxylate: 2,3-Dioxo-butyric acid tert-butyl ester (0.293 g, 1.54 mmol) and 4-iodo-2-methoxy-pyridine-3-carbaldehyde (0.405 g, 1.54 mmol) were reacted as described for the synthesis of 2-(4-iodo-2-methoxy-pyridin-3-yl)-5-methyl-3H-imidazole-4-carboxylic acid ethyl ester to give the title material (0.303 g, 47%). $^1$H NMR (400 MHz, DMSO-d6) δ (ppm) 1.58 (s, 9H) 2.46 (s, 3H) 3.85 (s, 3H) 7.64 (d, J=5.31 Hz, 1H) 8.00 (d, J=5.31 Hz, 1H).

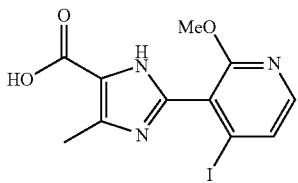

2-(4-Iodo-2-methoxypyridin-3-yl)-4-methyl-1H-imidazole-5-carboxylic acid: A stirred solution of tert-butyl 2-(4-iodo-2-methoxypyridin-3-yl)-4-methyl-1H-imidazole-5-carboxylate (0.047 g, 0.1131 mmol) in dichloromethane (0.8 mL) was added trifluoroacetic acid (0.6 mL) and the reaction was stirred at room temperature overnight. The solvent was evaporated after adding toluene (1 mL) and the residue was purified on Prep HPLC (trifluoroacetic acid/acetonitrile/water) to give the title material (0.039 g, 96%). $^1$H NMR (400 MHz, MeOH-d4) δ (ppm): 2.70 (s, 3H) 3.97 (s, 3H) 7.70 (d, J=5.56 Hz, 1H) 8.11 (d, J=5.56 Hz, 1H).

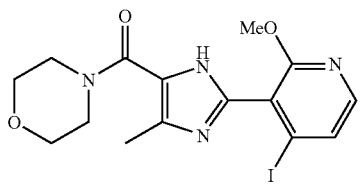

(2-(4-iodo-2-methoxypyridin-3-yl)-4-methyl-1H-imidazol-5-yl)(morpholino)methanone: To a stirred solution of 2-(4-iodo-2-methoxypyridin-3-yl)-4-methyl-1H-imidazole-5-carboxylic acid (0.039 g, 0.1085 mmol) in N,N-diemthylformamide (2 mL) was added triethylamine (60 mL, 0.434 mmol), morpholine (14 mL, 0.1627 mmol) and PyBOP (85 mgs, 0.1627 mmol) at room temperature. The reaction was stirred at room temperature for 10 minutes then the solvent was evaporated. The residue was dissolved in ethyl acetate and washed with water and brine. The organic layer was dried over anhydrous magnesium sulfate, filtered and concentrated. The residue was purified on Prep HPLC (ammonium acetate/acetonitrile/water) to give the title material (0.024 g, 52%). $^1$H NMR (400 MHz, DMSO-d6) δ (ppm): 2.32 (s, 3H) 3.54 (s, 8H) 3.76 (s, 3H) 7.55 (d, J=5.31 Hz, 1H) 7.87 (d, J=5.31 Hz, 1H).

EXAMPLE 1

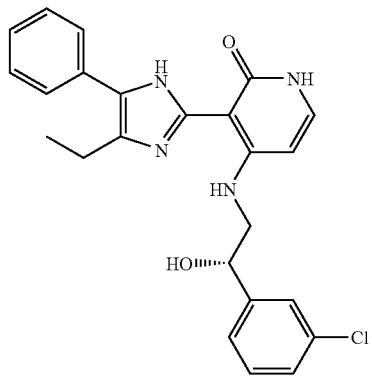

4-[2-(3-Chloro-phenyl)-2-hydroxy-ethylamino]-3-(4-ethyl-5-phenyl-1H-imidazol-2-yl)-1H-pyridin-2-one: 4-Ethyl-2-(4-iodo-2-methoxy-pyridin-3-yl)-5-phenyl-imidazol-1-ol (0.379 g, 0.90 mmol) was dissolved in acetic acid/hydrochloric acid (2 ml/2 mL) and the resulting mixture was stirred at 95° C. for 1 hour. The solvent was evaporated and the crude residue (HPLC 95% (220 nm), LCMS ($^+$ESI, M+H$^+$) m/z 408) was dissolved in methanol (6 mL) and treated with titanium (III) chloride (9.25 wt % in 27.4 wt % hydrochloric acid, ~1 mL). The reaction was heated at 65° C. for ~2.5 hours, then water was added and the solvent was evaporated to give a residue (HPLC 83% (220 nm), LCMS ($^+$ESI, M+H$^+$) m/z 392) which was dissolved in N,N-dimethylformamide (6 mL). The resulting solution was treated with triethylamine (0.38 mL, 2.7 mmol) and the hydrochloric acid salt of (S)-2-amino-1-[3-chlorophenyl]ethanol (0.281 g, 1.35 mmol) and this was heated at 65° C. for 4 hours. The solvent was evaporated and the residue was purified by Prep HPLC (ammonium acetate/acetonitrile/water) to give the title compound (0.132 g, 34%) as a beige solid. HPLC 97.5% (220 nm), LCMS (+ESI, M+H$^+$) m/z 435; IR ν (cm$^{-1}$): 3261, 2965, 1642; $^1$H NMR (400 MHz, methanol-d$_4$) δ (ppm): 1.36 (3H, t, J=7.5 Hz), 2.97 (2H, qa, J=7.5 Hz), 3.64 (1H, dd, J=13.5 and 6.9 Hz), 3.70 (1H, dd, J=13.7 and 5.0 Hz), 4.97 (1H, br t), 6.25 (1H, d, J=7.5 Hz), 7.21-7.33 (4H, m), 7.35-7.47 (4H, m), 7.52 (1H, s), 7.69 (1H, d).

EXAMPLE 2

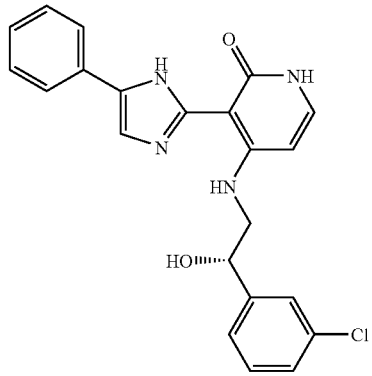

4-[2-(3-chloro-phenyl)-2-hydroxy-ethylamino]-3-(5-phenyl-1H-imnidazol-2-yl)-1H-pyridin-2-one: 4-Iodo-2-methoxy-3-(5-phenyl-1H-imidazol-2-yl)-pyridine (0.020 g, 0.053 mmol) was dissolved in acetic acid (1 mL) and concentrated hydrochloric acid (1 mL) and the mixture was refluxed for 2 hours. The solvent was evaporated to give a mixture of two compounds (0.019 g, iodo and chloro analogs, LCMS ($^+$ESI, M+H$^+$) m/z 272 and 364).

This mixture was dissolved in N,N-dimethylformamide (3 mL) and treated with triethylamine (20 μL, 0.159 mmol) and the hydrochloric acid salt of (S)-2-amino-1-[3-chlorophenyl] ethanol (0.022 g, 0.106 mmol). This mixture was heated at 80° C. for 3 hours, then the solvent was evaporated. The residue was purified by Prep HPLC (ammonium acetate/water/acetonitrile) to give the title material (0.007 g, 32%) as a yellow solid. HPLC 98.5% (220 nm), LCMS (⁺ESI, M+H⁺) m/z 407; IR ν (cm⁻¹): 3377, 1644; HRMS calcd for $C_{22}H_{20}N_4O_2Cl$ (M+H)⁺=407.1275, found: 407.1295;

¹H NMR (400 MHz, methanol-$d_4$) δ (ppm): 3.66 (1H, dd, J=13.7 and 7.1 Hz), 3.75 (1H, dd, J=13.7 and 5.3 Hz), 5.02 (1H, m), 6.27 (1H, d, J=7.5 Hz), 7.18-7.56 (10H, m), 7.84 (1H, d, J=7.0 Hz).

EXAMPLE 3

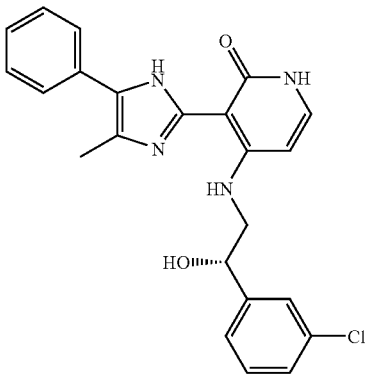

4-[2-(3-Chloro-phenyl)-2-hydroxy-ethylamino]-3-(4-methyl-5-phenyl-1H-imidazol-2-yl)-1H-pyridin-2-one: 2-(4-Iodo-2-methoxy-pyridin-3-yl)-4-methyl-5-phenyl-imidazol-1-ol (0.093 g, 0.228 mmol) was reacted as described for the synthesis of 4-[2-(3-chloro-phenyl)-2-hydroxy-ethylamino]-3-(4-ethyl-5-phenyl-1H-imidazol-2-yl)-1H-pyridin-2-one except that the compound was first treated with titanium(III) chloride and then hydrochloric acid/acetic acid. The title material was obtained (0.013 g, 14%) as a brown solid. HPLC 90.4% (220 nm), LCMS (⁺ESI, M+H⁺) m/z 421; IR ν (cm⁻¹): 3276, 2920, 1643; HRMS calcd for $C_{23}H_{22}N_4O_2Cl$=421.1431, found: 421.1409; ¹H NMR (400 MHz, methanol-$d_4$) δ (ppm): 2.54 (3H, g), 3.64 (1H, dd, J=13.5 and 7.1 Hz), 3.70 (1H, dd, J=13.5 and 5.1 Hz), 4.97 (1H, t, J=5.8 Hz), 6.25 (1H, d, J=7.5 Hz), 7.21-7.68 (1OH, m), 7.71 (1H, d, J=8.0 Hz).

EXAMPLE 4

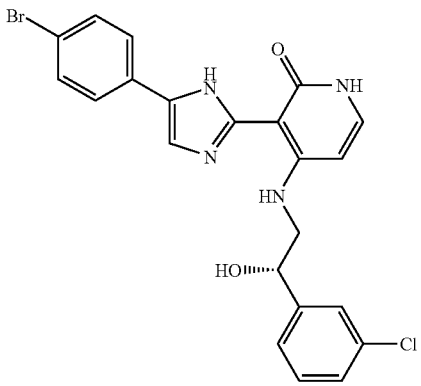

3-[5-(4-Bromo-phenyl)-1H-imidazol-2-yl]-4-[2-(3-chloro-phenyl)-2-hydroxy-ethylamino]-1H-pyridin-2-one: To a stirred solution of 3-[5-(4-bromo-phenyl)-1-hydroxy-1H-imidazol-2-yl]-4-[2-(3-chloro-phenyl)-2-hydroxy-ethylamino]-1H-pyridin-2-one (0.015 g, 0.030 mmol) in methanol (4 mL) was treated with titanium(III) chloride ((9.25 wt % in 27.4 wt % hydrochloric acid, ~200 µL). The reaction was heated at 65° C. for 1 hour, then quenched with water and the solvents were evaporated. The residue was purified by Prep HPLC (ammonium acetate/acetonitrile/water) to give the title material (0.006 g, 41%) as a beige solid. HPLC 100% (220 nm), LCMS (⁺ESI, M+H⁺) m/z 485,487, (⁻ESI, M−H⁻) m/z 483, 485; ¹H NMR (400 MHz, methanol-$d_4$) δ (ppm): 3.64 (1H, dd, J=13.3 and 7.1 Hz), 3.74 (1H, dd, J=13.3 and 4.5 Hz), 5.03 (1H, m), 6.26 (1H, d, J=7.5 Hz), 7.23-7.56 (9H, m), 7.77 (1H, d, J=8.6 Hz).

EXAMPLE 5

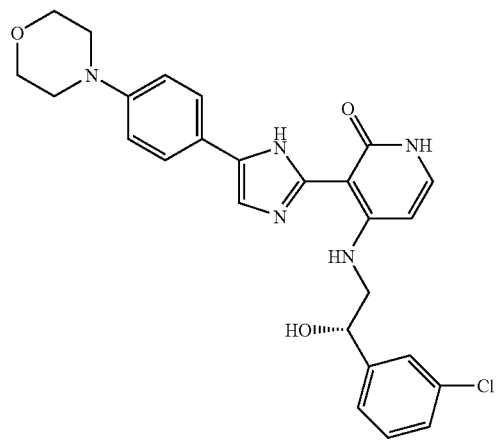

4-[2-(3-Chloro-phenyl)-2-hydroxy-ethylamino]-3-[5-(4-morpholin-4-yl-phenyl)-1H-imidazol-2-yl]-1H-pyridin-2-one: 2-(4-Iodo-2-methoxy-pyridin-3-yl)-5-(4-morpholin-4-yl-phenyl)-imidazol-1-ol (0.049 g, 0.102 mmol) was reacted as described for the synthesis of 4-[2-(3-chloro-phenyl)-2-hydroxy-ethylamino]-3-(4-ethyl-5-phenyl-1H-imidazol-2-yl)-1H-pyridin-2-one except that the compound was first treated with titanium(III) chloride LCMS (⁺ESI, M+H⁺) m/z 463) and then hydrochloric acid/acetic acid. The title material was obtained (0.007 g, 14%) as a yellow solid. HPLC 85% (220 nm), LCMS (⁺ESI, M+H⁺) m/z 492; ¹H NMR (400 MHz, methanol-$d_4$) δ (ppm): 3.18 (4H, br t), 3.65 (1H, br dd), 3.74 (1H, br dd), 3.87 (4H, m), 5.02 (1H, m), 6.26 (1H, d, J=7.5 Hz), 7.02 (2H, d, J=8.6 Hz), 7.22-7.56 (7H, m), 7.74 (1H, d, J=7.9 Hz).

EXAMPLE 6

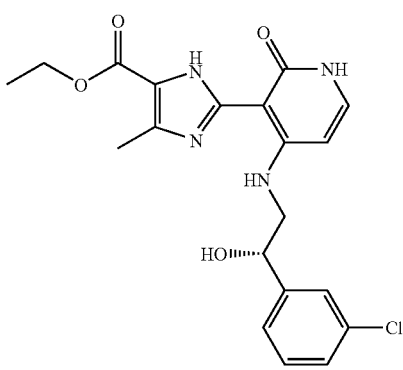

2-{4-[2-(3-Chloro-phenyl)-2-hydroxy-ethylamino]-2-oxo-1,2-dihydro-pyridin-3-yl}-5-methyl-3H-imidazole-4-carboxylic acid ethyl ester: 2-(4-Iodo-2-methoxy-pyridin-3-yl)-5-methyl-3H-imidazole-4-carboxylic acid ethyl ester (0.020 g, 0.052 mmol) was dissolved in acetic acid (1 mL) and concentrated hydrochloric acid (1 mL) and this mixture was stirred at reflux for 2 hours. The mixture was then evaporated and the residue was dissolved in N,N-dimethylformamide (2 mL) and treated with triethylamine (~22 µL, 0.155 mmol) and the hydrochloric acid salt of (S)-2-amino-1-[3-chlorophenyl] ethanol (0.020 g, 0.096 mmol). The mixture was heated at 65° C. overnight, then the solvent was evaporated and the residue was purified by Prep HPLC (ammonium acetate/acetonitrile/ water) to give the title compound (0.003 g, 14%) as a white solid. HPLC 100% (220 nm), LCMS (⁺ESI, M+H⁺) m/z 417; $^1$H NMR (400 MHz, methanol-$d_4$) δ (ppm) (mixture of tautomers): 1.40 and 1.43 (3H, 2t, J=7.1 Hz), 2.49 and 2.61 (3H, 2s), 3.61-3.72 (2H, m), 4.35 and 4.39 (2H, q, J=7.1 Hz), 4.95-4.97 (1H, m), 6.21 and 6.23 (1H, 2d, J=7.6 Hz), 7.19-7.55 (5H, m).

EXAMPLE 7

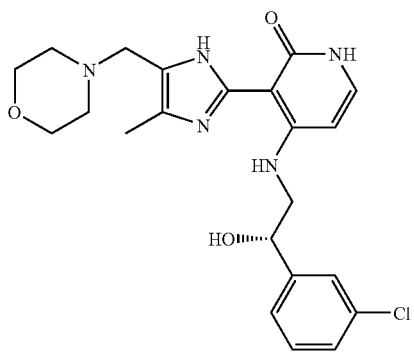

(S)-4-(2-(3-chlorophenyl)-2-hydroxyethylamino)-3-(4-methyl-5-(morpholinomethyl)-1H-imidazol-2-yl)pyridin-2(1H)-one: 4-((2-(4-Iodo-2-methoxypyridin-3-yl)-4-methyl-1H-imidazol-5-yl)methyl)morpholine (0.008 g, 0.019 mmol) was dissolved in acetic acid (2 mL) and concentrated hydrochloric acid (2 mL) and this mixture was stirred at 90° C. for 2 hours. The mixture was then evaporated and the residue was dissolved in 1-methyl-2-pyrrolidone (4 mL) and treated with triethylamine (100 µL, 0.72 mmol) and the hydrochloric acid salt of (S)-2-amino-1-[3-chlorophenyl]ethanol (0.010 g, 0.048 mmol). The mixture was heated at 90° C. for 4 hours, then the solvent was evaporated and the residue was purified by Prep HPLC (ammonium acetate/acetonitrile/water) to give the title compound (0.001 g, 11%) as a white solid. HPLC<95% (220 nm), LCMS (⁺ESI, M+H⁺) m/z 444; $^1$H NMR (400 MHz, methanol-$d_4$) δ (ppm): 2.21 (3H, br s), 2.56 (~4H, br s), 3.46 (2H, br s), 3.49 (1H, dd, J=6.8 and 13.6 Hz), 3.55 (1H, dd, J=5.3 and 13.6 Hz), 3.61 (4H, br s), 4.79-4.84 (1H, m overlapped by $D_2O$), 6.08 (1H, d, J=7.3 Hz), 7.06 (1H, d, J=7.6 Hz), 7.16 (1H, dt, J=8.4 and 1.8 Hz), 7.20 (1J, t, J=7.7 Hz), 7.27 (1H, br d, J=8.3 Hz), 7.39 (1H, br s).

EXAMPLE 8

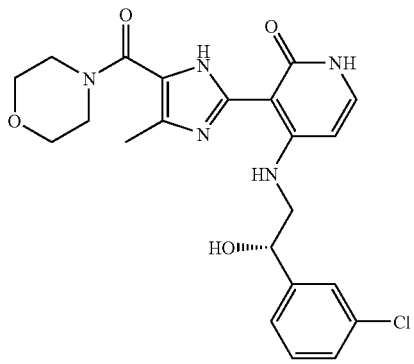

(S)-4-(2-(3-chlorophenyl)-2-hydroxyethylamino)-3-(4-methyl-5-(morpholine-4-carbonyl)-1H-imidazol-2-yl)pyridin-2(1H)-one: (2-(4-Iodo-2-methoxypyridin-3-yl)-4-methyl-1H-imidazol-5-yl)(morpholino)methanone (0.007 g, 0.017 mmol) was dissolved in acetic acid (1 mL) and concentrated hydrochloric acid (1 mL) and this mixture was stirred at 100° C. for 1 hour. The mixture was then evaporated and the residue was dissolved in N,N-dimethylformamide (2 mL) and treated with triethylamine (100 µL, 0.72 mmol) and the hydrochloric acid salt of (S)-2-amino-1-[3-chlorophenyl] ethanol (0.010 g, 0.048 mmol). The mixture was heated at 90° C. for 4 hours, then the solvent was evaporated and the residue was purified by Prep HPLC (ammonium acetate/acetonitrile/ water) to give the title compound (0.002 g, 25%) as a white solid. HPLC 100% (220 nm), LCMS (⁺ESI, M+H⁺) m/z 458; $^1$H NMR (400 MHz, methanol-$d_4$) δ (ppm): 2.37 (3H, s), 3.45-4.0 (10H, m), 4.7-4.9 (1H, m, overlapped by $D_2O$), 6.10 (1H, d, J=7.8 Hz), 7.10 (1H, d, J=7.6 Hz), 7.14-7.24 (3H, m), 7.36 (1H, s), 10.26 (1H, br s).

It is understood that the examples described above in no way serve to limit the true scope of this invention, but rather are presented for illustrative purposes. All references cited herein are incorporated by reference in their entirety.

What is claimed is:
1. A compound having the formula:

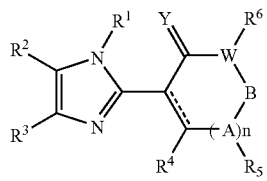

its enantiomers, diastereomers, or pharmaceutically acceptable salts thereof wherein:

n is 1;

Y is O or S;

A and B are independently —CH or CO, provided that A and B are not both CO;

W is N;

$R^1$, $R^3$, and $R^6$ are each H or $C_1$ to $C_6$ alkyl;

$R^2$ is H, $C_{1-6}$ alkyl, $C_{2-6}$ alkenyl, $C_{2-6}$ alkynyl, $C_{3-6}$ cycloalkyl, halo, amino, aminoalkyl, alkoxy, thioalkoxy, nitro, aryl, alkoxyalkyl, thioalkoxyalkyl, aralkyl, —CN, —C(O)$R^8$, —CO$_2R^8$, —CONR$^9R^{10}$, —CO$_2$NR$^{11}R^{12}$, —NR$^{13}$CONR$^{14}R^{15}$, —NR$^{16}$SO$_2R^{17}$, —SO$_2$NR$^{18}R^{19}$, —C(NR$^{20}$)NR$^{21}R^{22}$;

$R^4$ and $R^5$ are each H, —NH-Z, —NH-Z-aryl, wherein Z is selected from the group consisting of $C_1$-$C_4$ alkyl, alkenyl, and alkynyl; Z optionally having one or more hydroxy, thiol, alkoxy, thioalkoxy, amino, halo, NR$^{23}$SO$_2R^{24}$, —CO, —CNOH, —CNOR$^{26}$, —CNNR$^{27}$, —CNNCOR$^{28}$ and —CNNSO$_2R^{29}$; and $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and $R^{26}$ are independently selected from the group consisting of H, alkyl, alkenyl, alkynyl, cycloalkyl, cycloalkylalkyl, hydroxy, alkoxy, aryl, and alkyl-$R^{25}$ wherein $R^{25}$ is alkenyl, hydroxy, thiol, alkoxy, thioalkoxy, amino, alkylamino, dialkylamino, aryl, cyano, halo, sulfoxy, sulfonyl, —NR$^{27}$COOR$^{28}$, —NR$^{29}$C(O)R$^{30}$, —NR$^{31}$SO$_2R^{32}$, SO$_2$NR$^{31}R^{32}$—C(O)NR$^{33}R^{34}$, and $R^{27}$, $R^{28}$, $R^{29}$, $R^{30}$, $R^{31}$, $R^{32}$, $R^{33}$ and $R^{34}$ are, independently, hydrogen, alkyl, or cycloalkyl.

2. The compound of claim 1 wherein A and B are —CH.

3. The compound of claim 1 wherein $R^3$ is H, methyl, or ethyl.

4. The compound of claim 1 wherein $R^4$ is —NH-Z-aryl.

5. The compound of claim 1 wherein Y is O; $R^1$, $R^3$, $R^5$, $R^6$ are each independently H or $C_{1-6}$ alkyl; $R^2$ is aryl, or cycloalkyl; and $R^4$ is —NH-Z-aryl.

6. The compound of claim 1 wherein $R^2$ is an aryl, —C(O)$_2$-alkyl, or —CONR$^9$R$^{10}$ wherein $R^9$ and $R^{10}$ are independently H, $C_{1-6}$ alkyl, cycloalkyl, cycloalkylalkyl, aryl, or alkyl-$R^{25}$.

7. The compound of claim 6 wherein said aryl is a phenyl substituted with halo.

8. The compound of claim 6 wherein $R^2$ is lower alkyl or —C(O)R$^8$.

9. The compound according to claim 6 wherein $R^2$ is —C(O)$_2$alkyl.

10. The compound according to claim 9 wherein said alkyl is methyl, ethyl, or propyl.

11. A pharmaceutical composition comprising the compound of claim 1 in a pharmaceutically acceptable carrier.

12. A compound selected from the group consisting of
  4-[2-(3-Chloro-phenyl)-2-hydroxy-ethylamino]-3-(4-ethyl-5-phenyl-1H-imidazol-2-yl)-1H-pyridin-2-one;
  4-[2-(3-chloro-phenyl)-2-hydroxy-ethylamino]-3-(5-phenyl-1H-imidazol-2-yl)-1H-pyridin-2-one;
  4-[2-(3-Chloro-phenyl)-2-hydroxy-ethylamino]-3-(4-methyl-5-phenyl-1H-imidazol-2-yl)-1H-pyridin-2-one;
  3-[5-(4-Bromo-phenyl)-1H-imidazol-2-yl]-4-[2-(3-chloro-phenyl)-2-hydroxy-ethylamino]-1H-pyridin-2-one; and
  2-{4-[2-(3-Chloro-phenyl)-2-hydroxy-ethylamino]-2-oxo-1,2-dihydro-pyridin-3-yl}-5-methyl-3H-imidazole-4-carboxylic acid ethyl ester.

* * * * *